United States Patent [19]

Aufenanger

[11] Patent Number: 5,385,828
[45] Date of Patent: Jan. 31, 1995

[54] METHOD FOR DETERMINING THE RELATIVE AMOUNTS OF ALL CHOLESTEROL-CONTAINING LIPOPROTEINS IN BODY FLUIDS

[75] Inventor: Johannes Aufenanger, Hirschberg, Germany

[73] Assignee: "Immuno" Aktiengesellschaft fur chemisch-medizinische Produkte, Vienna, Austria

[21] Appl. No.: 981,992

[22] Filed: Nov. 24, 1992

Related U.S. Application Data

[63] Continuation of Ser. No. 359,800, Jun. 1, 1989, abandoned.

[51] Int. Cl.⁶ .................. C12Q 1/60; C12Q 1/34; C12Q 1/44; C12Q 1/26
[52] U.S. Cl. .................................. 435/11; 435/4; 435/15; 435/18; 435/19; 435/20; 435/21; 435/25; 435/26; 435/28; 435/183; 435/189; 435/190; 435/193; 435/194; 435/198; 435/232; 435/810; 435/817; 435/874
[58] Field of Search .................. 435/4, 11, 15, 18-21, 435/25, 26, 28, 183, 189, 190, 193, 194, 198, 232, 253, 810, 817, 874

[56] References Cited

U.S. PATENT DOCUMENTS

| | | | |
|---|---|---|---|
| 4,105,521 | 8/1978 | Golias | 204/180 |
| 4,491,631 | 1/1985 | Imamura et al. | 435/4 |
| 4,746,605 | 5/1988 | Kerscher et al. | 435/7 |

FOREIGN PATENT DOCUMENTS

| | | |
|---|---|---|
| 0183381 | 6/1986 | European Pat. Off. . |
| 3817747 | 11/1989 | Germany . |
| 58-210000 | of 1983 | Japan . |
| WO82/00833 | 3/1982 | WIPO . |

OTHER PUBLICATIONS

Principles of Enzymatic Analysis, edited by Hans Ulrich Bergmeyer, Verlag Chemie, Weinhein/New York (1978).
Oda et al, Chemical Abstracts, vol. 92, 1980, p. 258, #211170t.
The Condensed Chemical Dictionary, 1977, pp. 258, 642.
Biochem. Methods 102:163379u (1985).
Chem. Abstracts 92:211170t (1980).
Biochem. Methods 94:60909d (1981).
"Numbering and Classification of Enzymes", Principles of Enzymatic Analysis, H. Bergmeyer and K. Gawehn, eds., Verlag Chemie, Weinhein/New York 1978.
"Staining of lipoprotein fractions", Biochem. Methods 102, Abstract No. 163379u (1985).
Aufenanger et al., "A specific method for the direct determination of lipoprotein cholesterol in electrophoretic patterns", Biochem. Methods 109:421, Abstract No. 226121w (1988).
Hohenwallner et al., "Reference range of lipoprotein fractons determined by Lipidophor", Biochem. Methods 94:313, Abstract No. 60909d (1981).
Hohenwallner et al., "Reference values of lipoprotein fractions determined by Lipidophor", Arztl. Lab. 26:293-295 (1980).
Oda et al., "High-density lipoprotein cholesterol estimated by a thin layer Agarose gel film electrophoresis", Rinsho Byori 27(12):1142-1146 (1979) (with English translation).

Primary Examiner—Mindy B. Fleisher
Attorney, Agent, or Firm—Sterne, Kessler, Goldstein & Fox

[57] ABSTRACT

The invention refers to a method for determining the relative amounts of all cholesterol-containing lipoproteins in body fluids comprising electrophoretically separating the lipoproteins of an aliquot of body fluid on a thin layer carrier matrix, incubating the carrier matrix, containing the separated lipoproteins with cholesterol esterase and cholesterol dehydrogenase, forming a provable complex, and determining the relative amounts of the different lipoprotein classes2. The new method makes it possible to simultaneously determine HDL-, LDL-, VLDL- and LP (X)-cholesterol in body fluids with a high accuracy even at small concentrations. The thin layer matrices obtained electrophoretically, are very easy to handle and to record.

29 Claims, No Drawings

METHOD FOR DETERMINING THE RELATIVE AMOUNTS OF ALL CHOLESTEROL-CONTAINING LIPOPROTEINS IN BODY FLUIDS

This application is a continuation, of application Ser. No. 07/359,800, abandoned filed Jun. 1, 1989.

DESCRIPTION

The invention refers to a method for determining the relative amounts of all cholesterol-containing lipoproteins in body fluids as well as to a method for determining the cholesterol concentration of these lipoproteins.

Numerous studies (Lipid Research Clinics Coronary Primary Prevention Trial, 1984, Helsinki Heart Study, 1987, Multiple Risk Factor Intervention Trial (MRFIT-study), 1986, Gottinger Coronary Study 1980, Kasseler Prospective Study, since 1981), prove the relationship between lipoprotein metabolism disturbances and the origins of atherosclerosis and myocardial infarct. In many previous studies (Framingham study, 1977), only the HDL (High-Density-Lipoprotein)-cholesterol was regarded as a significant factor in the origin or atherosclerosis, from which it was assumed that is the most sensitive factor for the risk of coronary heart disease for men and women over 50. However, previous studies always refer to the fact that the actual decisive parameter is the ratio of LDL (low-density lipoprotein) cholesterol and HDL cholesterol. This ratio, the so-called atherogenic quotient, describes the ratio or the disproportion of lipoproteins, which are brought by the liver as LDL into the periphery (vessels of other organs) and are transported back to the liver again as HDL. Today, it serves as the basis for an individual risk evaluation.

The determination of HDL cholesterol and LDL cholesterol thus assumes a great importance in the evaluation of the individual fat metabolism risk. In the state of the art, efforts have been made for years to make fast and reliable methods available for the separation and determination of cholesterol in different lipoprotein fractions. The classical separation method is ultracentrifuging. However, this method is not useable for routine analyses, because first it is very time consuming and secondly it requires costly equipment. In addition, precipitation methods and electrophoretic methods have been developed for separation of the main lipoprotein classes, namely HDL cholesterol and LDL cholesterol, according to alpha and beta lipoproteins.

For example, in the state of the art, electrophoretically separated lipoproteins have been dyed with lipid-dyes such as for example Sudan black B and fat red 7 B; however, these dyes color all lipids unspecifically and are not specific for cholesterol and cholesterol esters.

More specific, more recent methods propose the incubation of electrophoretically separated lipoprotein factions with a developer solution, which contains enzymes specifically reacting with cholesterol, for example cholesterol esterase and cholesterol oxidase. So a method for proving cholesterol lipoproteins is known from DE-OS 28 40 680, in which the lipoproteins separated on a cellulose acetate matrix are incubated in a solution of a cholesterol esterase and cholesterol oxidase. The method of the DE-OS 28 40 680 finally leads to a quinone imino complex, which is very easily water soluble and fades very rapidly. In addition, the method is not very precise, linear only to a range of 1.5 g/l cholesterol/fraction and thus principally useable to prove the HDL cholesterol. For the simultaneous proof of several lipoprotein classes, for example VLDL (Very-Low-Density-Lipoprotein), LDL and HDL, different thinned out specimens must be applied; the cholesterol content of chylomicrons can not be determined with this method.

In Japanese publication no. 58-210000 (1983), corresponding to Japanese Patent 57-92731 a method is described which provides the proof of cholesterol with the use of cholesterol esterase and cholesterol dehydrogenase; the occurring water-insoluble formazane complexes are formed in a gel. The proof system proposed in this application requires very long electrophoresis times and developmental times and is very expensive due to a very high requirement of costly enzymes and is unusable for routine studies; in addition, the results are extremely difficult to record.

In German patent application P 36 40 349.0-41, a method is described which makes it possible to greatly reduce the costs involved in the method described in the named Japanese patent publication. The rate and the ability to record however can be improved.

Thus the present invention is based on the task of developing a method of the type named at the outset, which allows a rapid and reliable determination of all diagnostically relevant lipoprotein fractions within a short time, whereby the method can also be reproduced and the result should be able to be recorded.

This task is solved in a method of the type named at the outset where electrophoresis is carried out on a thin layer matrix.

It is possible with the method according to the invention to reliably determine the relative amounts of all lipoprotein fractions from any bodily fluids within a very short time, for example plasma or serum and one can even reliably analyze specimens from heparinized patients. The reaction on which the method according to the invention is based provides for the dehydrogenation of cholesterols released from lipoproteins to Δ5-cholesten-3-one by transmitting electrons of cholesterol via NAD+/NADH +H + to an electron coupler, for example PMS, and from there to a last electron acceptor, preferably tetrazolium salt. This reaction chain leads to the formation of a stable, water-insoluble formazane complex, which can be determined densitometrically in the thin layer matrix. The atherogenic quotient, the ratio of LDL-cholesterol in HDL cholesterol, can subsequently be formed directly from the densitometric surface integrals of both lipoprotein fractions. It was very surprising with the use of thin layer matrices, and also with the separation of only one μl of the actual body fluid, to find completely sufficient amounts of formed complexes at the actual positions of the matrix. This was surprising, because the expert had expected to find an amount of the primary electron donor insufficient for the formation of the formazane complex, namely of the cholesterol, in the thin layer matrix.

However, surprisingly, extremely small amounts of cholesterol can be determined reliably with the method according to the invention. The lower boundary of proof lies at only 5 ng per trace and band. First, HDL-, LDL-, VLDL- and Lp(X) cholesterol can be determined side by side and with high precision with the method according to the invention. The cholesterol concentrations can be determined exactly in the range of 50-3200 mg/l body fluid.

The formazane complex formed in the method according to the invention is extremely difficult to dissolve in water. This has the advantage that an already formed complex diffuses little in a relatively little concentrated matrix and the resulting bands are thus very sharply differentiated. In addition, the formed formazane complex is very light resistant and thus, can be proven after an ample time with high reproducibility and with the same intensity. It has been shown that even at very high cholesterol concentrations of bodily fluid used for the electrophoresis, the formed formazane complex does not crystallize out with drying of the thin layer matrix, but even in the dried matrix leads to a sharp, densitometrically very good evaluatable band now as before.

Carrier matrices of all kinds can be used for carrying out the method according to the invention, preferably agarose and polyacrylamide. Both matrix materials are on the market in quality sufficient for the method according to the invention. The only requirement made on the used matrix is that it be free of stabilizers and enzyme inhibitors, which could endanger the enzymatic conversion taking place subsequent to electrophoresis. In addition, the matrix should be useable for thin layer electrophoresis, so that a somewhat stable matrix can form in the desired thickness. The specimen application on the matrix takes place, for example, with the aid of a slotted foil. The applied specimen volume preferably amounts to about 5 $\mu$l and diffuses within an acceptable time of about 10 min into the matrix. Of course the specimen volume can also be increased or decreased as a function of the slot dimensions and time.

In a preferred design form, an 0.8 to 1.2 wt. % agarose gel in a suitable buffer is used as matrix. This gel should exhibit a thickness of $0.1 \propto 0.5$ mm, preferably 0.35 mm.

Up to about 0.5 wt. % albumin is mixed with the gel, in order to promote the homogeneity of the bands. Human serum albumin as well as cattle serum albumin preparations or others can be used. The use of albumin is not essential; however, it makes the bands more homogeneous, which leads to a very simple quantitative evaluation.

The method according to the invention provides that the thin layer matrix is brought into contact with a developer solution after electrophoresis, enabling the cholesterol-containing lipoprotein bands of the actually electrophoretically separated liquid to be proven. In addition to cholesterol esterase and cholesterol dehydrogenase, this developer solution contains the coenzyme nicotinamide-adenine dinvcleotide of the cholesterol dehydrogenase, an electron coupler and a color indicator. Thereby, the cholesterol esterase causes a splitting off of the cholesterol from the cholesterol ester in the actual lipoprotein, the cholesterol dehydrogenase causes a dehydrogenation to cholesten-3-one the electron coupler takes up the electrons transmitted with dehydrogenation of the cholesterol in the form of a hydride ion to the nicotinamide-adenine dinvcleotide and by means of this co-oxidizes the coenzyme again, and finally, the transfer of the electrons onto a suitable color indicator leads to the formation of a provable color complex. As a rule, the developer solution contains the usual additives, for example buffering substances, in order to be able to carry out the reaction in the range of the pH-optimum of the participating enzymes and in the given case a chelate former which in the given case, by complexing of present metal ions, for example $Mg^{2+}$ or $Zn^{2+}$, inhibits proteases dependent on the presence of these metal ions.

Preferred buffer systems in this connection are tris(-hydroxymethyl)aminomethane (tris), barbital or a mixture thereof. A preferred pH-range to be adjusted lies between 7.8 and 8.6.

Two basically different possibilities are provided with the selection of a suitable electron coupler to carry out the method according to the invention. The use of an enzymatic electron coupler, namely of the enzyme diaphorase is known from the Japanese patent publication 58-210000 (1983). By means of this, however, another biological substance is introduced into the method which, like every enzyme, exhibits a lower stability and a greater sensitivity than an organic chemical substance. Therefore, phenazine methosulfate (PMS) is preferably used as electron coupler.

The color indicator finally reduced by the reaction is tetrazolium salt according to the invention, preferably nitro blue tetrazolium chloride (NTB) or 2-(p-iodine phenyl-3-(p-nitrophenyl)-5-phenyltetrazolium chloride (INT). In principle, any tetrazolium salt can be used, however, preferably it should exhibit a high molar extinction coefficient in order not to endanger the sensitivity of the method according to the invention.

In a preferred design form of the method according to the invention, the developer solution contains the following substances:

Tris-HCL-buffer: 30–60 mM, preferably 57 mM
NAD: 0.2–2.0 mM, preferably 0.5 mM
EDTA: 0.05–0.2 mM, preferably 0.1 mM
NTB or INT: 0.05–3.0 nM, preferably 0.16 mM
PMS: 0.01–0.05 mM, preferably 0.03 mM
at a pH of: 7.8–8.6, preferably pH 8.0,
Cholesterol esterase: 0.2–1.0 U/ml, preferably 0.4 U/ml
Cholesterol dehydrogenase: 0.07–1.0 U/ml, preferably 0.14 U/ml The method according to the invention achieves its highest sensitivity with the use of the listed substances in the given concentration ranges.

The concentrations of the individual components used in the method according to the invention, especially of the used enzyme, lies clearly below the one indicated in Japanese patent publication No. 58,210000 (1983). This is to be essentially attributed to the use of the thin layer matrix, in which the lipoprotein-cholesterol molecule can be better achieved by diffusion.

The development of the thin layer matrix in the developer solution can take place at 37° for about 45 min, but it can also be carried out at room temperature. A development at room temperature runs somewhat more slowly. In this case 2 h time should be given to the reaction.

A special advantage of the method according to the invention is that the developed thin layer matrix can be dried according to the method known in the state of the art. The matrix which in connection for example with physicians' reports has a documentary character, on the one hand can be better managed and thus can be more easily evaluated, and on the other hand can be comfortably recorded. These characteristics represent a very essential advantage of the method according to the invention over the method from the state of the art.

The evaluation of the developed thin layer matrix takes place according to a likewise known method, e.g. densitometrically. The wavelength used for densitometry depends on the selection of the last electron acceptor and for example amounts to 570 nm in the case of the use of INT, and in the case of the use of NTB it amounts to 546 nm. It is obvious that the wavelength of its absorption maximum for densitometry is used for each alternatively used tetrazolium salt.

According to the invention, in addition to the method for determining the relative amounts of all cholesterol-containing lipoproteins in body fluids, a method is made available to determine the cholesterol concentration of all cholesterol containing lipoproteins in body fluids. This method of the total cholesterol content of the actual specimen is determined according to a method known in the state of the art and the relative fractions of the different cholesterol-containing lipoproteins obtained by densitometric evaluation is related to this total amount. In this way the absolute values of concentrations of different lipoprotein fractions can be determined in the body fluids of a patient.

The following example explains the invention:

EXAMPLE 1

Production of Thin Layer Agarose Gels 0.1 g agarose (standard EEO (electroendoosmosis) was suspended well in 10 ml barbital glycine buffer (50 mmol/l, pH 8.6) and boiled for 30 min in a reflux condenser. After cooling the solution to 60° C., 0.02 g albumin was dissolved in it.

To produce a gel, 2 ml of this agarose solution was applied to prepared gel carrier foils (Gelfond, Serva-Heidelberg; 7×8 cm) on a warmed levelling table (60° C.) by means of a preheated pipette and uniformly distributed. This agarose was then allowed to cool and gel under dust-free conditions. After gelling, the gel was covered with a foil and allowed to harden before use overnight in a refrigerator.

Carrying out of the Electrophoresis

The protective foil was removed from the gel and the gel was laid on a horizontal base. Excessive moisture was removed from the gel surface by applying a gel blotter (filter paper). Subsequently a test mask was applied (slotted mask with 6 slots 8×0.5 mm) in the first third of the gel and this was lightly pressed on so that no more air bubbles could be seen under the mask.

5 μl serum of different patients were applied to the specimen slits and allowed to diffuse into the gel for 10 minutes. After 10 min diffusion time, non diffused in specimen was carefully suctioned up with the specimen blotter (filter paper strip) and the slotted mask was subsequently carefully removed.

The gel was then suspended in a foil holder in such a way that the gel layer pointed down. The foil assumed the form of a round arc.

The foil holder with the suspended gel was set on the electrode carrier of the electrophoresis chamber filled with the electrode buffer (see below). The gel ends jutted about 0.5 cm into the buffer.

The specimens were separated by 40 minute electrophoresis (90 v).

Electrode buffer for electrophoresis:
1 L barbital-glycine buffer (50 mmole/1, pH 8.6)

Carrying out Enzymatic Treatment

The following stock solutions were produced for the enzymatic treatment:

I. Buffer A (modified tris-buffer, 0.3 M)

Dissolve 18.2 g trishydroxymethylaminomethane in 400 ml bidistilled water and adjust to pH 8.0 with 1N HCl; add 4 ml TRITON X-100 and 0.5 ml DMSO (dimethysulfoxide), then fill to 500 ml with bidistilled water.

II. Phenazinemethosulfate (PMS), 3.27 mM Dissolve 100 mg PMS in 100 ml bidistilled water.

III. Nitroblue-Tetrazolium-Chloride (NTB) Dissolve 100 mg NTB in 100 ml bidistilled water.

IV. nicotinamide-adenine dinuleotide (NAD), 13 mM Dissolve 1000 mg NAD in 10 ml diluted buffer A (diluted 1:4 with bidistilled water).

V. Ethylenediaminetetraacetic acid-dihydrate (disodium salt), 10 mM

Dissolve 372 mg EDTA.2H$_2$O in 100 ml bidistilled water.

VI. Cholesterol-Dehydrogenase (45.2 U/ml)

VII. Cholesterol-Esterase 52 U/ml

Shortly before the expiration of electrophoresis, the reaction mixture was prepared as follows:

The following were pipetted from the stock solutions in a dye cuvette (size 7.5×8.5 cm, light impermeable):

| | |
|---|---|
| Buffer A, pH 8.0 | 1.25 ml |
| NAD | 0.25 ml |
| EDTA | 0.06 ml |
| NTB | 0.60 ml |
| PMS | 0.06 ml |
| Cholesterol dehydrogenase | 0.02 ml |
| Cholesterol esterase | 0.05 ml |
| Bidistilled water | 4.4 ml |

After the conclusion of electrophoresis, the gel foil was laid in the dye cuvette and incubated by means of a "gel swing" under light movements for 2 h at room temperature.

After incubation, the gel was removed from the reaction mixture and rinsed from both sides with distilled water. The violet color of the cholesterol-containing bands was clearly visible. This gel exhibited several sharp, strong bands.

The lower side of the foil was dried with a soft cellulose cloth and each individual track was densitometered in the gel densitometer at 546 nm. The gel was laid in 1% acetic acid 30 min after the evaluation for the purpose of recording (washing out the photosensitive rests of PMS and NTB) and subsequently dried dust free at room temperature. A densitometric determination of the bands carried out for comparison purposes after drying gave no essential deviations from the previously obtained result.

Quantification of the Cholesterol Content in the Lipoprotein Bands

The cholesterol content of the individual lipoprotein fractions was determined after determining the total cholesterol content of the applied specimens (enzymatic cholesterol determination by means of cholesterol oxidase-peroxidase method). Thus the following values were determined for one of the patients:

Total cholesterol content in the serum: 200 mg/dl

Densitometric expression:
  beta-lipoprotein (LDL)-cholesterol band: 60%
  pre-beta-lipoprotein (VLDL)-cholesterol band: 10%
  alpha-lipoprotein (HDL)-cholesterol bands: 30%

From this follows:

| | |
|---|---|
| LDL-cholesterol | 120 mg/dl |
| VLDL-cholesterol | 20 mg/dl |

| -continued | |
|---|---|
| HDL-cholesterol | 60 mg/dl |

I claim:

1. A method for simultaneously determining the amount of a cholesterol-containing lipoprotein selected from the group consisting of very low density lipoproteins, low density lipoproteins, and high density lipoproteins contained in a body fluid relative to the amount of at least one other of said cholesterol-containing lipoproteins or the total amount of cholesterol-containing lipoproteins present in said body fluid comprising the steps of:
  (a) electrophoretically separating the cholesterol-containing lipoproteins contained in a body fluid from one another on a thin layer carrier matrix comprising albumin, said albumin being present in a concentration of UP to about 0.5 % by weight;
  (b) incubating said carrier matrix, following separation of said cholesterol-containing lipoproteins, in the presence of a developer solution comprising cholesterol esterase at a concentration of 0.02–2.0 U/ml and cholesterol dehydrogenase at a concentration of 0.07–1.0 U/ml; and
  (c) determining the relative amounts of said cholesterol-containing lipoproteins.

2. The method of claim 1, wherein said thin layer carrier matrix comprises polyacrylamide or agarose.

3. The method of claims 1 or 2, wherein the thin layer carrier matrix comprises 0.8 to 1.2 weight % agarose and has a thickness of 0.1 to 0.5 mm.

4. The method of claim 1, wherein said developer solution further comprises nicotinamide-adenine dinucleotide (NAD), an electron coupler, and a tetrazolium salt color indicator.

5. The method of claim 4, wherein said developer solution further comprises a buffer.

6. The method of claim 5, wherein said buffer is tris(-hydroxymethyl)aminomethane (Tris), barbital or a mixture thereof.

7. The method of claim 4, wherein said electron coupler is phenazine methosulfate (PMS) or diaphorase.

8. The method of claim 4, wherein said tetrazolium salt color indicator is selected from the group consisting of nitroblue tetrazolium chloride (NTB) , and 2-(p-iodinephenyl)-3-(p-nitrophenyl)-5-phenyltetrazolium chloride (INT).

9. The method of claim 1, wherein said thin layer carrier matrix is developed and dried prior to the determination step.

10. The method of claim 1, wherein the determination step is a densitometric evaluation.

11. The method of claim 10, wherein said densitometric evaluation is carried out at 570 nm with use of therefor 2-(p-iodinephenyl)-3-(p-nitrophenyl)-5-phenyltetrazolium chloride (INT).

12. The method of claim 10, wherein said densitometric evaluation is carried out at 546 nm with use of nitroblue tatrazolium choride (NTB).

13. The method of claim 4 wherein said developer solution comprises Tris-HCl-buffer; nicotinamide-adenine dinucleotide; ethylenediaminetetraacetic acid; nitroblue tetrazolium chloride, or 2-(p-iodinephenyl)-3-(p-nitrophenyl)-5-phenyltetrazoliumchloride; phenazinemethosulfate; cholesterol dehydrogenase at a concentration of 0.07–1.0 U/ml; and cholesterol esterase at a concentration of 0.02–2.0 U/ml.

14. The method of claim 13 wherein said Tris-HCl-buffer has a pH of 7.8–8.6.

15. The method of claim 14 wherein said Tris-HCl-buffer has a pH of 8.0.

16. The method of claim 13 wherein said Tris-HCl-buffer is at a concentration of 30–60 mM.

17. The method of claim 16 wherein said Tris-HCl-buffer is at a concentration of 57 mM.

18. The method of claim 13 wherein said nicotinamide-adenine dinucleotide is at a concentration of 0.2–2.0 mM.

19. The method of claim 18 wherein said nicotinamide-adenine dinucleotide at a concentration of 0.5 mM.

20. The method of claim 13 wherein said ethylenediaminetetraacetic acid is at a concentration of 0.05–0.2 mM.

21. The method of claim 20 wherein said ethylenediaminetetraacetic acid is at a concentration of 0.1 mM.

22. The method of claim 13 wherein said nitroblue tetrazolium chloride or 2-(p-iodinephenyl)-3-(p-nitrophenyl)-5-phenyltetrazolium chloride is at a concentration of 0.05–3.0 mM.

23. The method of claim 22 wherein said nitroblue tetrazolium chloride or 2-(p-iodinephenyl)-3-(p-nitrophenyl)-5-phenyltetrazolium chloride is at a concentration of 0.16 mM.

24. The method of claim 13 wherein said phenazine methosulfate is at a concentration of 0.01–0.05 mM.

25. The method of claim 24 wherein said phenazine methosulfate is at a concentration of 0.03 mM.

26. The method of claim 1 wherein said cholesterol dehydrogenase is at a concentration of 0.14 U/ml.

27. The method of claim 1 wherein said cholesterol esterase is at a concentration of 0.4 U/ml.

28. A method for simultaneously determining the amount of a cholesterol-containing lipoprotein selected from the group consisting of very low density lipoproteins, low density lipoproteins, and high density lipoproteins contained in a body fluid relative to the amount of at least one other of said cholesterol-containing lipoproteins or the total amount of cholesterol-containing lipoproteins present in said body fluid comprising the steps of:
  (a) electrophoretically separating the cholesterol-containing lipoproteins contained in a body fluid from one another on a thin layer carrier matrix having a thickness of 0.1 to 0.5 mm and consisting essentially of:
    (1) albumin, said albumin being present in a concentration of up to about 0.5% by weight, and
    (2) agarose or polyacrylamide;
  (b) incubating said carrier matrix, following separation of said cholesterol-containing lipoproteins, in the presence of a developer solution comprising:
    (1) cholesterol esterase at a concentration of 0.02–2.0 U/ml;
    (2) cholesterol dehydrogenase at a concentration of 0.07–1.0 U/ml;
    (3) tris(hydroxymethyl)aminomethane (Tris) buffer at a concentration of 30–60 mM;
    (4) nicotinamide-adenine dinucleotide (NAD) at a concentration of 0.2–2.0 mM;
    (5) phenazine methosulfate (PMS) at a concentration of 0.01–0.05 mM;
    (6) EDTA at a concentration of 0.05–0.2 mM; and
    (7) a tetrazolium salt color indicator selected from the group consisting of nitroblue tetrazolium chloride (NTB) and 2-(p-iodinephenyl)-3-(p-nitrophenyl)-5-phenyltetrazolium chloride (INT) at a concentration of 0.05–3.0 mM; and (c) determining the relative amounts of said cholesterol-containing lipoproteins.

29. The method of claim 28, wherein said developer solution comprises: 57 mM Tris-HCl-buffer, pH 8.0; 0.5 mM NAD; 0.1 mM EDTA; 0.16 mM NTB or INT; 0.03 mM PMS; 0.14 U/ml cholesterol dehydrogenase; and 0.4 U/ml cholesterol esterase.

* * * * *

UNITED STATES PATENT AND TRADEMARK OFFICE
CERTIFICATE OF CORRECTION

PATENT NO. : 5,385,828
DATED : January 31, 1995
INVENTOR(S) : Aufenanger

It is certified that error appears in the above-indentified patent and that said Letters Patent is hereby corrected as shown below:

On the title page, Item [56],

Under the heading "Other Publications", Column 2, line 16, delete "fractons" and insert therein --fractions--;

Column 1, line 52, delete "7 B" and insert therein --7B--;
    line 57, delete "factions" and insert therein --fractions--;

Column 3, line 35, delete "0.1 $\propto$ 0.5" and insert therein --0.1-0.5--;
    line 51, delete "dinvcleotide" and insert therein --dinucleotide--;
    line 59, delete "dinvcleotide" and insert therein --dinucleotide--;

Column 4, line 50, between "37°" and "for" insert therein --C--;

Column 7, claim 11, lines 2 to 3, delete "therefor";
    claim 12, line 3, delete "tatrazolium choride" and insert therein --tetrazolium chloride--; and
    claim 13, line 2, between "solution" and "comprises" insert --further--.

Signed and Sealed this

Thirty-first Day of October 1995

Attest:

BRUCE LEHMAN

*Attesting Officer*    *Commissioner of Patents and Trademarks*